United States Patent
Laukkanen et al.

(10) Patent No.: US 8,693,619 B2
(45) Date of Patent: Apr. 8, 2014

(54) MEDICAL COMPUTED TOMOGRAPHY IMAGING APPARATUS

(75) Inventors: Tapio Laukkanen, Espoo (FI); Sami Tohka, Porvoo (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 13/695,101

(22) PCT Filed: Apr. 29, 2011

(86) PCT No.: PCT/FI2011/050394
§ 371 (c)(1),
(2), (4) Date: Oct. 29, 2012

(87) PCT Pub. No.: WO2011/135193
PCT Pub. Date: Nov. 3, 2011

(65) Prior Publication Data
US 2013/0051518 A1    Feb. 28, 2013

(30) Foreign Application Priority Data
Apr. 29, 2010   (FI) ..................... 20100180
Sep. 30, 2010   (FI) ..................... 20100336

(51) Int. Cl.
*H05G 1/02*   (2006.01)
*H05G 1/00*   (2006.01)

(52) U.S. Cl.
USPC ............... 378/4; 378/193; 378/204; 378/210

(58) Field of Classification Search
USPC ........ 378/4–20, 193–198, 204, 205, 208, 210
See application file for complete search history.

(56) References Cited

U.S. PATENT DOCUMENTS

| | | | |
|---|---|---|---|
| 6,315,445 B1 * | 11/2001 | Mazess et al. | 378/196 |
| 6,435,717 B1 * | 8/2002 | Kohler et al. | 378/206 |
| 7,016,465 B2 * | 3/2006 | Kamegawa | 378/63 |
| 7,108,421 B2 | 9/2006 | Gregerson et al. | |
| 7,170,967 B2 | 1/2007 | Cherek et al. | |
| 7,388,941 B2 | 6/2008 | Sukovic et al. | |
| 7,433,503 B2 | 10/2008 | Cherek et al. | |
| 2002/0118280 A1 | 8/2002 | Medlar et al. | |
| 2004/0081341 A1 | 4/2004 | Cherek et al. | |
| 2006/0074286 A1 | 4/2006 | Miller et al. | |
| 2006/0079763 A1 | 4/2006 | Jeung et al. | |
| 2007/0053486 A1 | 3/2007 | Zelnik et al. | |
| 2007/0244384 A1 | 10/2007 | Gore | |
| 2010/0059679 A1 | 3/2010 | Albrecht | |

FOREIGN PATENT DOCUMENTS

| | | |
|---|---|---|
| JP | 201012319 | 1/2010 |
| WO | 2006039394 A2 | 4/2006 |

* cited by examiner

*Primary Examiner* — Anastasia Midkiff
(74) *Attorney, Agent, or Firm* — Fay Sharpe LLP

(57) ABSTRACT

The invention relates to a medical computed tomography imaging apparatus which includes a support construction (1) which is arranged to support a substantially ring-shaped structure (2) supporting x-ray imaging means (21, 22), which x-ray imaging means (21, 22) are arranged within said substantially ring-shaped structure supporting the imaging means (2) and movable within said substantially ring-shaped structure supporting the imaging means (2), which ring-shaped structure (2) supporting the imaging means (21, 22) includes an examination opening (4), whereto the object to be imaged can be positioned for imaging. According to the invention, at least one display (11) is arranged to the apparatus. The display is arranged in functional connection with at least one video camera (12), which at least one video camera (12) is arranged in connection with said ring-shaped structure (2) and as aimed, or so that it can be aimed inside said examination opening (4).

19 Claims, 2 Drawing Sheets

MEDICAL COMPUTED TOMOGRAPHY IMAGING APPARATUS

FIELD OF INVENTION

The invention relates to a medical imaging apparatus according to the preamble of claim 1.

BACKGROUND OF INVENTION

Conventional apparatuses employed in medical x-ray imaging most simple of their basic structure comprise a source of radiation which is used together with a film cassette separate from the source of radiation. Hospitals commonly use also the so-called C-arch x-ray apparatuses where the source of radiation and the receiver of image information are arranged at the opposite ends of the arched arm part. Conventionally, a device group of its own consists of large-size and extremely expensive computed tomography apparatuses where the patient is typically positioned for imaging in the recumbent position within a ring-shaped or tubular structure.

Computed tomography apparatuses have also been developed into more lightweight versions. As an example of prior art arrangements, we refer to U.S. Pat. Nos. 7,108,421 and 7,388,941. In such apparatuses, imaging means rotatable for 360 degrees around the imaging station are arranged within a ring-shaped O-arm supported from the side. The O-arm may be arranged adjustable for its height position and turnable with respect to a horizontal axis.

As conventional computed tomography apparatuses have been quite massive and expensive, acquiring them e.g. for the use of hospital emergency rooms has not been possible in practice. On the other hand, it is also typical for commercial computed tomography apparatuses that they are not necessarily designed for imaging some specific anatomy or anatomies but they are more or less general imaging apparatuses. If e.g. desiring to image the patient's whole torso, the imaging station to be arranged to the apparatus as well as other dimensions of the apparatus have had to be implemented in respective proportions.

BRIEF DESCRIPTION OF INVENTION

The object of the present invention is to advance the state of the art concerning x-ray imaging apparatuses, especially the ones less expensive and of smaller size referred to above as compared to the conventional computed tomography apparatuses. The embodiments of the invention preferably offer a possibility to implement a cone-beam computed tomography imaging apparatus particularly designed applicable for imaging extremities, for example, the properties and price of which could bring purchase of the apparatus within resources available for e.g. emergency clinics. As the conventional computed tomography employs a narrow fan-like beam, in cone-beam tomography the beam is collimated to be genuinely two-dimensional but often to cover only a quite small specific area (volume) of the object being imaged. A special object of the invention is to advance development particularly in the field of x-ray imaging apparatuses comprising a ring-shaped arm part of the above-described type, the construction, characteristics and dimensions of which differ in many respects from the conventional hospital computed tomography apparatuses and in which the patient is positioned for imaging in another way than in conventional computed tomography apparatuses, whereto the patient is positioned lying on the imaging tray.

Especially, the object of the invention is an arrangement that offers good visibility to the imaging area and by which e.g. patient positioning can thus be facilitated in connection with imaging lower extremities and, on the other hand, ease off the phobia the patient may have concerning the imaging.

Essential characteristics of the invention are described in the accompanying patent claims. Especially essential for the invention is a display arranged e.g. to the outer cover of the ring-shaped so-called O-arm of the above-described type or elsewhere in connection with the imaging apparatus, which display is arranged in functional connection with a camera arranged in connection with said arm for shooting images of the imaging station of the apparatus. The display may be connected with the control system of the apparatus, and via said display the patient can be shown information and instructions how to act on, such as information of the exact time of initiation of the exposure, for the patient to remain stationary, or for how many seconds the exposure will still last. By the invention and its preferable embodiments, also the working ergonomics can be improved as while positioning the patient's extremity, one does not necessarily have to bend down to the imaging area to be able see whether it is properly positioned.

Next, the invention and its preferable embodiments will be described in more detail also with reference to the enclosed figures.

DETAILED DESCRIPTION OF INVENTION

In the following, the terms centre and central axis will be used in connection with structures which do not necessarily form a true, full circle but are of circular shape only for their prevailing part. To avoid ambiguity, these terms refer in connection with this specification to a point and an axis which would be the centre or central axis of the structure in question in case that structure would form a full circle.

Furthermore, concerning one component of the apparatus according to the invention, this specification employs terms a substantially ring-shaped structure and an O-arm. When the dimension in the direction of the central axis of this structure can be significantly large with respect to the diameter of the ring-shaped structure in question, for the avoidance of doubt it is stated that in the following, vertical position of the O-arm refers to a position where the central axis of the O-arm is horizontally oriented and horizontal position of the O-arm refers to a position where its central axis is vertically oriented.

Figure 1:
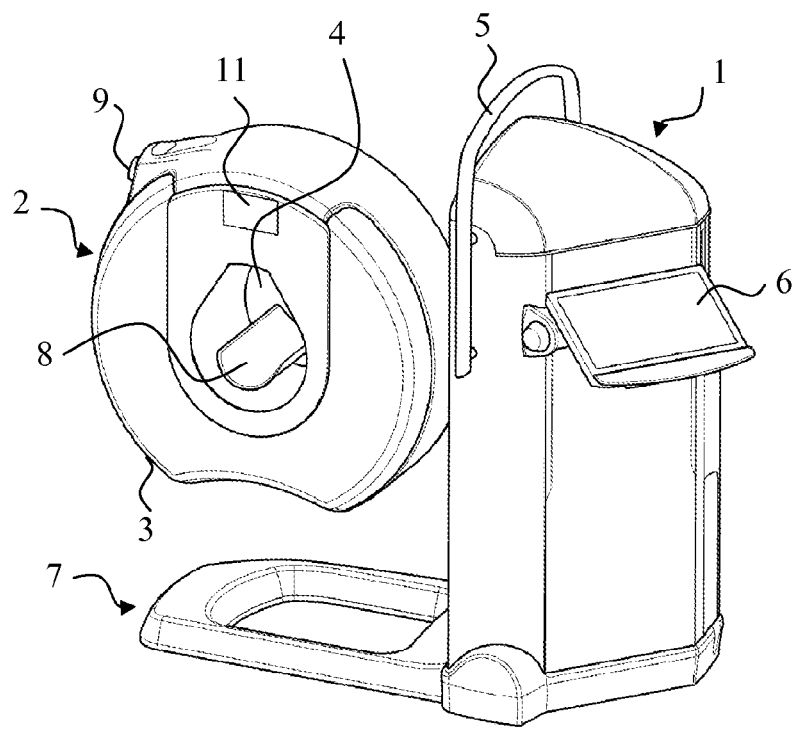
FIG. 1 shows a general view of one imaging apparatus according to the invention, its basic structure including a support construction as well as a substantially ring-shaped O-arm and a display arranged in connection with it.

FIG. 1 shows a general view of one imaging apparatus according to the invention. The basic structure of the apparatus includes a support construction (1) which supports a substantially ring-shaped structure (2) within which x-ray imaging means (21, 22) of the apparatus are located and which is also referred to as an O-arm in this context. This O-arm (2) is arranged with an examination opening (4) within which an anatomy to be imaged is positioned. FIG. 1 further shows a patient support rail (5) arranged to the support construction (1), a user interface (6) being in functional connection with a control system of the apparatus, a possibly detachably attached pedestal or base part (7) projecting substantially in the direction of the O-arm, and a positioning support (8) arranged to the examination opening (4). According to the embodiment of the invention shown in FIG. 1, the display (11) belonging to the apparatus is arranged substantially on the surface of the ring-shaped structure (2), at its upper edge.

Mounting of the structure (2) supporting the imaging means to the support construction (1) can be arranged to enable adjustment of the height position of the O-arm (2). Furthermore, this O-arm (2) can be arranged to be turnable in at least one direction for at least 90 degrees from the vertical position shown in FIG. 1) to the horizontal position. The control of these manoeuvres can be arranged implementable aside from the user interface (6) being connected with the control system of the apparatus also by means of a joy stick (9) arranged into connection with the O-arm (2) and/or the support frame (1).

When looking at the cross-section perpendicular to the direction of the central axis of the O-arm (2) shown in FIG. 1, i.e. the radial cross-section of the O-arm (2), an outer cover (3) of the O-arm (2) forms for its prevailing part a circle which yet comprises a sector where the distance from the centre of said circle to the edges of the outer cover (3) is smaller than the radius of that portion being circular for its prevailing part. In the embodiment of the invention according to FIG. 1, the part in said sector being cut off the O-arm (2) is evenly curved in the opposite direction with respect to the arch of the circle of the prevailing portion of the outer cover (3), but this cut part can also be of some other shape, such as wedge-shaped, rectangular, straight or even curved in the same direction as the portion of the arch of the outer cover (3) substantially of the shape of a circle.

When a sector of the kind described above is arranged at a section of the O-arm (2) substantially orienting downwards or being orientable downwards, it can be easier to implement e.g. imaging of lower extremities in sitting position when thanks to the invention, the examination opening (4) can be driven closer to the floor level as compared to an O-arm (2) not comprising such a cut. On the other hand, if the imaging apparatus is provided with a possibility to adjust the height position of the O-arm (2) and to turn the O-arm (2) to a position where the central axis of the O-arm (2) is substantially vertical, one may use the apparatus to image the patient in a standing position, too. Then, said cut arranged to the O-arm (2) makes it easier for the patient to step into the examination opening (4) and out of the examination opening as the length of the step one needs to take over the 'doorstep' formed by the O-arm (2) will be shorter.

In the embodiment of the invention according to FIG. 1, the examination opening (4) is implemented only for its prevailing part substantially as a circle. A sector has been arranged to the examination opening (4) which forms an extension to the circle. That is, the examination opening (4) is provided with a sector in the area of which the distance of the edge of the examination opening (4) from the centre of the circular portion of the examination opening (4) (or from the central axis of the O-arm (2)) is longer than the radius of the circular portion of the examination opening (4). Such design of the examination opening (4) is preferable e.g. when the aim is to realize dimensions of the cross-section perpendicular with respect to the central axis of the O-arm structure as small as possible, such as when considering an embodiment basically designed for imaging anatomies having a smaller diameter than the diameter of the human torso, such as extremities.

Enlarging the examination opening (4) in some sector of the circle facilitates patient positioning e.g. when imaging a plastered leg. In such an embodiment of the invention we are talking about an examination opening (4) the diameter of the portion of the shape of an arch of a circle of which is e.g. of the order of 30-35 cm. In the embodiment according to FIG. 1, the examination opening (4) is substantially of the shape of a droplet, i.e. the shape of its extension is substantially an equilateral triangle having a truncated apex, but said extension can naturally be of some other shape as well.

Figure 2:
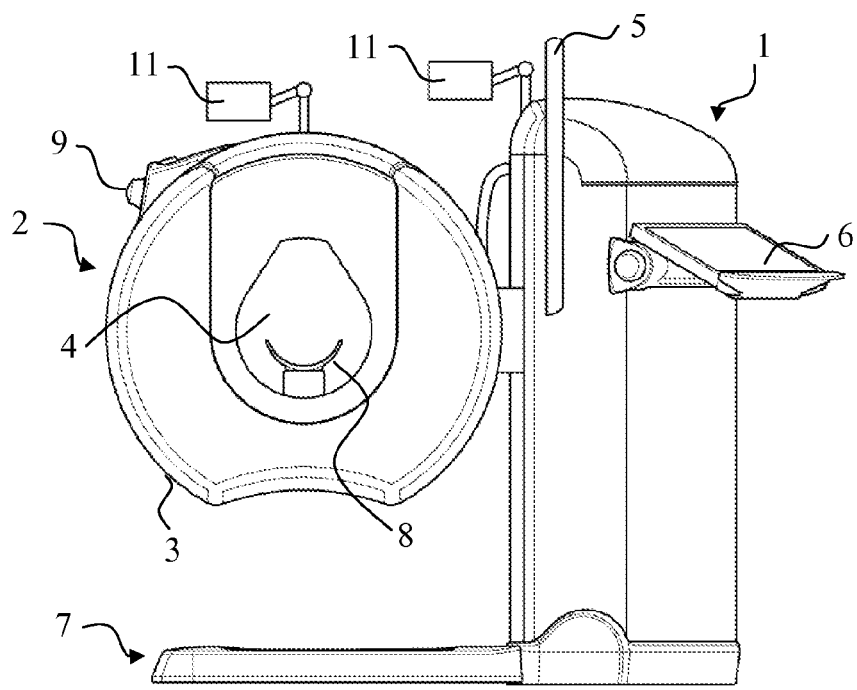
FIG. 2 shows two different solutions according to the invention for arranging a display to the apparatus.

As compared to FIG. 1, FIG. 2 shows two alternative ways to position the display (11) in connection with the apparatus. The display is preferably positioned to the apparatus at a location which is visible to the patient when e.g. patient's leg is being imaged. The display (11) can be arranged to the ring-shaped structure (2) both as fixed and as movably attached. The connection can be arranged to enable either adjusting orientation of the display (11) with respect to the ring-shaped structure (2), adjusting clearance and/or location of the display (11) with respect to the ring-shaped structure (2), or it can be arranged with some or all of these degrees of freedom of movement. Alternatively, the display (11) can be attached to the supporting structure (1), or an own separate display (11) can be arranged to the supporting structure (1), which display (11) can be arranged with the degrees of freedom of movement as described above but with respect to the supporting structure (1).

According to one preferable embodiment of the invention, the display (11) is arranged in functional connection with the control system of the apparatus for displaying e.g. imaging parameter values, like the exposure time of the imaging still left. This type of functional connection can also be arranged e.g. with a patient database. Guiding and informing of the patient of the different phases of the imaging facilitates successful imaging, correct positioning of the anatomy for imaging and, especially, the patient remaining still for the whole substantially long exposure.

According to the basic structure of the apparatus according to the invention, the x-ray imaging means, i.e. a source of x-radiation (21) and a receiver of x-ray image information (22), are arranged within the substantially ring-shaped structure (2) supporting the x-ray imaging means and as movable along a curved path within said structure, substantially on opposite sides of the examination opening (4), whereby the distance between the edge of the examination opening (4) and the outer cover (3) of the O-arm (2) (or the radial dimension of the ring of the O-arm) must naturally be arranged of adequate size to enable said paths. FIG. 2 shows a possible embodiment of the invention which includes a ring-shaped support part (20) arranged within the O-arm (2), whereto substantially on opposite sides from each other are arranged the source of x-ray radiation (21) and the receiver of x-ray image information (22). The support part (20) is arranged rotatable within the structure (2) supporting the x-ray imaging means by means of an actuator (23) and a transmission belt (24). Hence, it is possible to image the object positioned at the examination opening (4) from different directions within the range of the angle of rotation of the x-ray imaging means and to create of thus acquired image information a voxel model by means of image-data processing methods known as such.

Figure 3:
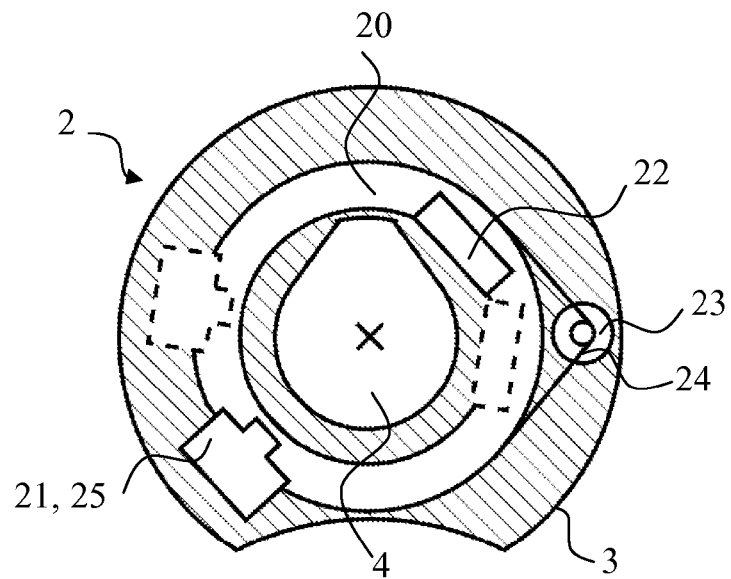
FIG. 3 shows one embodiment according to the invention for arranging x-ray imaging means used in computed tomography to a ring-shaped imaging part of the apparatus.

In the embodiment according to FIG. 3, the source of radiation (21) and the receiver of image information (22) are arranged movable within the substantially ring-shaped structure (2) supporting the imaging means with respect to a centre of rotation such that the source of radiation (21) (the focus of the source of radiation) moves at a different distance from said centre of rotation than the receiver of image information (22). In the arrangement according to FIG. 3, the source of radiation (21) is attached on the outer circumference of the ring-shaped support part (20) whereby, when rotating the support part (20), the focus of the source of radiation (21) moves farther from said centre of rotation than the receiver of image information (22) attached on the side of the inner circumference of the support part (20). When the receiver of image information (22) is thus brought closer to the volume being imaged, it is possible when using a detector (22) of given size to use a wider beam and thus increase the volume being imageable as compared to that the receiver of image information (22) were to move farther from the object.

According to one preferable embodiment of the invention, the range of movement of the imaging means is implemented unlike in some prior-art apparatuses of similar type, i.e. by arranging the source of radiation (21) and the receiver of image information (22) movable along a curved path substantially on opposite sides of the examination opening (4) for a shorter distance than 360 degrees. This distance is referred to in the context of this specification as an angle of rotation, and preferably it is arranged to be somewhat larger than 180 degrees but then substantially smaller than 360 degrees, such as of the order of 210+/−20 degrees. Then, arranging the imaging means (21, 22) to be movable at different distances from the centre of rotation may preferably be implemented particularly in an arrangement comprising the above-described cut in the O-arm (2) and extension in the examination opening (4). The range of manoeuvring of the source of radiation (21) can be arranged not to extend to that sector of the O-arm in which the outer cover (3) has been cut like described above and, on the other hand, the range of manoeuvring of the receiver of image information (22) not to extend to that sector of the O-arm (2) in which is arranged an extension of the examination opening (4) as described above. When the utmost dimensions of said extension and cut from the centre of rotation of the imaging means are arranged appropriate with respect to those different distances at which the imaging means are rotated from the centre of rotation, the apparatus can be implemented as shown in FIG. 3 such that the source of radiation (21) arranged to move farther from the centre of rotation is able to move outside the extension of the examination opening (4) and the receiver of image information (22), again, inside the cut arranged to the outer cover (3) of the O-arm (2).

Especially, such embodiment of the invention enables a structure where, e.g. considering imaging of extremities, due to the extension arranged to the examination opening (4) it is possible to implement the diameter of the circular portion of the examination opening (4) smaller than would be possible without the extension sector and, further, it is possible to arrange the cut to the outer cover (3) of the O-arm (2) which facilitates several positioning procedures of a patient. Such an embodiment of the invention is implementable as a compact structure and it enables realizing both the examination opening (4) and the outer dimensions of the whole O-arm (2) smaller than would otherwise be possible.

It was mentioned above that the extension arranged to the examination opening (4) facilitates e.g. positioning of a plastered leg to the examination opening. Placing the anatomy to be imaged to the examination opening (4) can be further facilitated by arranging the patient positioning support (8) arranged in connection with the examination opening (4) movable or detachably attached such that it is both positionable to a desired location within the examination opening (4) for imaging and positionable or transferrable to a place where it impedes patient positioning as little as possible. The purpose of such patient positioning support (8) is to assist positioning of the anatomy being imaged to a desired point with respect to the O-arm (2). Preferably, the patient positioning support (8) comprises a concave structure whereto an upper or a lower extremity can be positioned for the duration of the imaging.

The angle of rotation of the imaging means (21, 22) described above is sufficient in cone-beam tomography, in which the beam generated by the source of radiation (21) is arranged to be limited to a true two-dimensional beam and the receiver of image information (22), again, of its form and dimensions at least such that it covers said two-dimensional beam. In the apparatus according to the invention, such beam can also be arranged to be limited to more than one size and/or shape, whereby the receiver of image information (22) must naturally be arranged either to cover all possible beam sizes and shapes or it must be arranged changeable.

Figure 4:
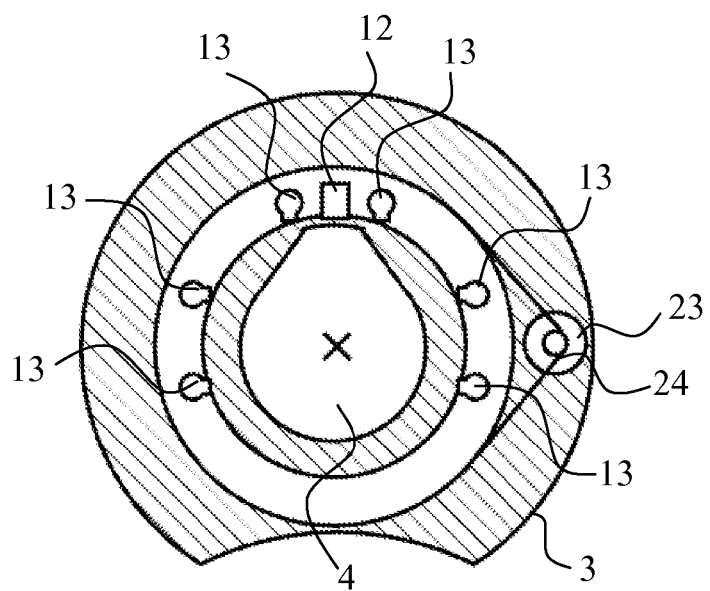
FIG. 4 shows, as simplified, how the structure according to FIG. 3 can be arranged with at least one camera and with positioning lights to be utilized in connection with positioning the anatomy to be imaged.

Positioning the object inside the examination opening (4), exactly at the desired place within the imaging area of the apparatus, can also be facilitated by arranging in the apparatus one or several video cameras (which term is used here to mean both a video camera and a photographic camera). In the embodiment presented in FIG. 4, one such video camera (12) is arranged in connection with the ring-shaped structure (2) of the apparatus as aimed (or so that it can be aimed) at inside the examination opening (4). In principle, the camera (4) can be arranged to the ring-shaped structure (2) outside its cover, particularly at the opposite side of the examination opening from which the extremity to be imaged is designed to be brought into the examination opening, but in a preferable embodiment of the invention, the video camera (12) is arranged within the ring-shaped structure (2) and at least part of the inside of the said ring-shaped structure (2) is arranged transparent or to contain a whole, through which the camera (12) is aimed at the examination opening (4), like substantially at a positioning support (8) arranged in the examination opening.

The apparatus can also be provided with positioning lights (13), which for their part further facilitate positioning of the anatomy to be imaged. Such lights (13) are arranged aiming towards said examination opening (4) to create a light pattern which facilitates the positioning, which light pattern can then be photographed, together with the anatomy being positioned, with at least one video camera (12) belonging to the apparatus, which photograph can then be displayed on said at least one display (11). Further, according to one preferable embodiment of the invention, the control system of the apparatus comprises means for adjusting the size and/or shape of said light pattern and, correspondingly, means for adjusting the size and/or shape of the x-ray beam, such as e.g. a collimator structure (25) arranged substantially in connection with the radiation source (21), which said means are brought into functional connection with each other either such that adjusting of the size and/or shape of the light pattern changes the size and/or shape of the x-ray beam, or such that adjusting the size and/or shape of the x-ray beam changes the size and/or shape of the light pattern.

In one preferable embodiment of the invention, the at least one camera (12) the apparatus comprises and/or at least a portion of the positioning lights are arranged to the same rotatable support part (20) to which the x-ray imaging means (21, 22) are attached.

The patient support rail (5) of the imaging apparatus shown in FIG. 1 is preferably arranged to extend from top of the support construction (1) substantially to at least one side of the support construction, especially to a side from the direction of which the patient is at least primarily thought to station oneself for imaging—i.e. preferably to the side in the direction of which the cut of the outer cover (3) of the O-arm (2) is arranged to be turned. The patient support rail (5) especially facilitates imaging in standing position, i.e. imagings where the O-arm (2) is turned into a position where its central axis is in the vertical orientation, when the patient can take support for himself/herself from the rail (5) when standing inside the O-arm (2) as well as when stepping in and out of it. In a preferable embodiment of the invention, the patient support rail (5) extends to at least one such side of the support construction (1) in the direction of which the cut sector arranged to the O-arm (2) is arranged to be turned.

The preferable embodiments of the invention described above can be implemented as a relatively compact structure and, for achieving many of the advantages described above, as a structure where the radius of the prevailing portion of the examination opening (4) being of the shape of an arch of a circle is of the order of 15 cm or slightly more and, on the other hand, the radius of the prevailing portion of the O-arm (2) of the shape of an arch of a circle is of the order of 50 cm or even less. Here, the distance of the focus of the source of radiation (21) from the centre of rotation of the imaging means (21, 22) can preferably be arranged e.g. for about 390 mm and that of the receiver of image information for about 190 mm. Thanks to the designs of the ring-shaped O-arm (2), and the video camera (12) and the display (11) arranged in connection with the apparatus, it becomes significantly easier for the patient to position oneself for imaging, and to position the anatomy to be imaged at the imaging area of the apparatus, especially in cases the patient as such is voluminous or handicapped, or in case some part of the patient's anatomy is so big that it tends to impede positioning of the anatomy desired to be imaged by the computed tomography arrangement within the imaging area of the apparatus.

It is obvious for one skilled in the art that as for its details, the present invention may be implemented also in other ways than according to the embodiments of the invention described above.

The invention claimed is:

1. A computed tomography imaging apparatus, which apparatus includes
   a support construction which is arranged to support a substantially ring-shaped structure supporting x-ray imaging means, which x-ray imaging means include a source of x-ray radiation and a receiver of image information, which x-ray imaging means are arranged within said substantially ring-shaped structure supporting the imaging means substantially on opposite sides of each other and movable within said ring-shaped structure supporting the imaging means,
   a control system for controlling at least part of the operations of the apparatus,
   which apparatus includes in said ring-shaped structure supporting the x-ray imaging means an examination opening wherein the object to be imaged is positionable for imaging, and in which apparatus said substantially ring-shaped structure supporting the x-ray imaging means is arranged movable with respect to said support construction at least in the vertical direction, characterized in that
   at least one display is disposed on the apparatus, which display is arranged in functional connection with at least one video camera, which at least one video camera is arranged in connection with said ring-shaped structure and is aimed or such that it may be aimed inside said examination opening.

2. An imaging apparatus according to claim 1, characterized in that said at least one display is placed on the apparatus at a location which is visible to the patient when the patient's leg is being imaged at a seated position.

3. An imaging apparatus according to claim 1, characterized in that said at least one display is arranged in functional connection with the control system of the apparatus for displaying imaging parameters.

4. A computed tomography imaging apparatus, which imaging apparatus includes
   a support construction which is arranged to support a substantially ring-shaped structure supporting x-ray imaging means, which x-ray imaging means include a source of x-ray radiation and a receiver of image information, which x-ray imaging means are arranged within said substantially ring-shaped structure supporting the imaging means substantially on opposite sides of each other and movable within said ring-shaped structure supporting the imaging means,
   a control system for controlling at least part of the operations of the apparatus,
   which apparatus includes in said ring-shaped structure supporting the x-ray imaging means an examination opening wherein the object to be imaged is positionable for imaging, and in which apparatus said substantially ring-shaped structure supporting the x-ray imaging means is arranged movable with respect to said support construction at least in the vertical direction, characterized in that
   at least one display forms a component of the apparatus, which display is arranged in functional connection with at least one video camera, which at least one video camera is arranged in connection with said ring-shaped structure and is aimed or such that it may be aimed inside said examination opening, and further
   characterized in that said at least one display is arranged to the apparatus as movably attached.

5. An imaging apparatus according to claim 1, characterized in that said at least one display is disposed on said ring-shaped structure or on said support structure.

6. An imaging apparatus according to claim 1, characterized in that said at least one display is disposed on said ring-shaped structure and movable such that its orientation with respect to said ring-shaped structure is adjustable.

7. A computed tomography imaging apparatus, which imaging apparatus includes
   a support construction which is arranged to support a substantially ring-shaped structure supporting x-ray imaging means, which x-ray imaging means include a source of x-ray radiation and a receiver of image information, which x-ray imaging means are arranged within said substantially ring-shaped structure supporting the imaging means substantially on opposite sides of each other and movable within said ring-shaped structure supporting the imaging means,
   a control system for controlling at least part of the operations of the apparatus,
   which apparatus includes in said ring-shaped structure supporting the x-ray imaging means an examination opening wherein the object to be imaged is positionable for imaging, and in which apparatus said substantially ring-shaped structure supporting the x-ray imaging means is arranged movable with respect to said support construction at least in the vertical direction, characterized in that at least one display forms a component of the apparatus, which display is arranged in functional connection with at least one video camera, which at least one video camera is arranged in connection with said ring-shaped structure and is aimed or such that it may be aimed inside said examination opening, and further characterized in that said at least one camera is arranged inside the ring-shaped structure and at least part of the inner surface of the said ring-shaped structure is arranged transparent or to comprise an opening, through which said at least one camera is aimed or can be aimed towards said examination opening.

8. An imaging apparatus according to claim 1, characterized in that a positioning support is at least partially located within said examination opening for positioning the anatomy to be imaged for x-ray imaging and said at least one camera is aimed or arranged to be aimed substantially towards said positioning support.

9. An imaging apparatus according to claim 1, characterized in that positioning lights which are aimed or can be aimed towards said examination opening are arranged to the apparatus, a light pattern formed by which is arranged to be photographed by said at least one camera and to be shown on said at least one display.

10. An imaging apparatus according to claim 9, characterized in that the control system of the apparatus comprises a means for adjusting size and/or shape of said light pattern and a means for adjusting size and/or shape of the x-ray beam, which said means are brought in mutual functional connection either such that adjusting the size and/or the shape of the light pattern changes the size and/or the shape of the x-ray beam, or such that adjusting the size and/or the shape of the x-ray beam changes the size and/or the shape of the light pattern.

11. An imaging apparatus according to claim 1, characterized in that said source of radiation and receiver of image information are arranged movable within said substantially ring-shaped structure supporting the imaging means with respect to a centre of rotation for an angle of rotation which is wider than 180 degrees and narrower than 360 degrees.

12. A computed tomography imaging apparatus, which imaging apparatus includes
 a support construction which is arranged to support a substantially ring-shaped structure supporting x-ray imaging means, which x-ray imaging means include a source of x-ray radiation and a receiver of image information, which x-ray imaging means are arranged within said substantially ring-shaped structure supporting the imaging means substantially on opposite sides of each other and movable within said ring-shaped structure supporting the imaging means,
 a control system for controlling at least part of the operations of the apparatus,
 which apparatus includes in said ring-shaped structure supporting the x-ray imaging means an examination opening wherein the object to be imaged is positionable for imaging, and in which apparatus said substantially ring-shaped structure supporting the x-ray imaging means is arranged movable with respect to said support construction at least in the vertical direction, characterized in that at least one display forms a component of the apparatus, which display is arranged in functional connection with at least one video camera, which at least one video camera is arranged in connection with said ring-shaped structure and is aimed or such that it may be aimed inside said examination opening, and further characterized in that said source of radiation and receiver of image information are arranged movable within said substantially ring-shaped structure supporting the imaging means with respect to a centre of rotation such that the source of radiation moves at a different distance from said centre of rotation than the receiver of image information.

13. An imaging apparatus according to claim 1, characterized in that a substantially ring-shaped support part is arranged within said ring-shaped structure supporting the imaging means, said source of radiation and receiver of image information are attached to said support part and said support part is arranged rotatable inside the structure supporting the imaging means.

14. An imaging apparatus according to claim 1, characterized in that a substantially ring-shaped support part is arranged within said ring-shaped structure supporting the imaging means as rotatable inside the ring-shaped structure supporting the imaging means, to which support part said at least one camera is attached.

15. An imaging apparatus according to claim 1, characterized in that the beam generated by the source of radiation is arranged to be limited to a true two-dimensional beam and the receiver of image information, again, of its form and dimensions for the least such that it covers said two-dimensional beam.

16. An imaging apparatus according to claim 1, characterized in that the radius of the prevailing portion of the examination opening being of the shape of an arch of a circle is of the order of 15 cm or slightly more, the radius of the prevailing portion of said structure supporting the imaging means being of the shape of an arch of a circle is of the order of 50 cm or less, and/or that the distance of the focus of the source of radiation from the centre of rotation of the imaging means is about 390 mm and the distance of the receiver of image information from the centre of rotation of the imaging means is about 190 mm.

17. An imaging apparatus according to claim 3, wherein said imaging parameter comprises exposure time remaining.

18. An imaging apparatus according to claim 11, characterized in that said source of radiation and receiver of image information are arranged movable within said substantially ring-shaped structure supporting the imaging means with respect to a centre of rotation for an angle of rotation which is wider than 180 degrees and narrower than 230 degrees.

19. An imaging apparatus according to claim 11, characterized in that said source of radiation and receiver of image information are arranged movable within said substantially ring-shaped structure supporting the imaging means with respect to a centre of rotation for an angle of rotation which is wider than 180 degrees and narrower than 190 degrees.

* * * * *